United States Patent [19]
Dunshee et al.

[11] Patent Number: 6,149,614
[45] Date of Patent: Nov. 21, 2000

[54] MEDICAL ADHESIVE COMPOSITE AND PACKAGE

[75] Inventors: Wayne K. Dunshee, Maplewood; Donald G. Peterson, Shoreview; Clarence A. Niven, Jr., White Bear Lake; John E. Riedel, Hugo, all of Minn.

[73] Assignee: Minnesota Mining and Manufacturing Company, St. Paul, Minn.

[21] Appl. No.: 08/887,523

[22] Filed: Jul. 2, 1997

Related U.S. Application Data

[63] Continuation-in-part of application No. 08/677,426, Jul. 2, 1996, abandoned.

[51] Int. Cl.⁷ .............................. A61F 13/00; A61F 15/00
[52] U.S. Cl. .............................. 602/57; 602/54; 602/900; 206/440
[58] Field of Search .................................. 602/48, 52, 54, 602/57–59, 900; 206/440, 441

[56] References Cited

U.S. PATENT DOCUMENTS

| Re. 24,906 | 12/1960 | Ulrich ........................................ 206/59 |
| Re. 33,353 | 9/1990 | Heinecke .................................. 428/40 |

(List continued on next page.)

FOREIGN PATENT DOCUMENTS

| 0 051 935 | 5/1982 | European Pat. Off. ......... A61F 13/02 |
| 0 066 899 | 12/1982 | European Pat. Off. ......... A61F 13/02 |
| 0 081 990 | 6/1983 | European Pat. Off. ......... A61F 13/02 |
| 0 124 732 | 11/1984 | European Pat. Off. ......... A61F 15/00 |
| 0 161 865 | 11/1985 | European Pat. Off. ......... A61F 13/02 |
| 0 236 104 | 9/1987 | European Pat. Off. ......... A61F 13/02 |
| 0 303 422 | 2/1989 | European Pat. Off. ......... A61F 13/00 |
| 0 465 023 | 1/1992 | European Pat. Off. ......... A61F 13/02 |
| 0 520 330 B1 | 12/1992 | European Pat. Off. . |

(List continued on next page.)

OTHER PUBLICATIONS

Flyer "Tegasorb™Ulcer Dressing"; Medical–Surgical Division 3M Health Care; Form no. 70–2008–2728–8 (301)ii; 1990.

Flyer "3M Tegasord™ THIN hydrocolloid dressing"; 3M Health Care; Form no. 70–2008–6475–2 (43.5)ii; 1993.

Flyer "3M Tegasorb™ ulcer dressing" Medical–Surgical Division 3M Health Care; Form no. 70–2008–5430–6(5115)VP; 1991.

Brochure "Wound Care"; Medical–Surgical Division 3M Health Care; Form no. 70–2008–4526–4(70.8)VP; Feb. 1990.

Flyer "3M Tegaderm™ 1624W transparent dressing"; 3M Health Care; Form no. 70–2008–6769–8(73.75)ii; 1993.

Flyer "3M Tegaderm Transparent Dressing"; 3M Health Care; Form no. 70–2008–7408–2(644)ii; 1994.

Brochure "Tegaderm™ Transparent Dressing—Suggested Applications and Special Techniques"; 3M Health Care; Form no. 70–2008–5413–4(321.5)11; Oct. 1991.

Fey et al., "Chapter 18—Silicone Release Coatings"; Handbood of Pressure–Sensitive Adhesive Technology; 1982; pp. 384–403.

Límová et al.; "Clinical Evaluation of Two Hydrocolloid Dressings in the Management of Venous Insufficiency Ulcers"; 3M Health Care; Form no. 70–200809650–7(76.25)ii; 1996.

Brochure "3M Tegasorb™ Hydrocolloid Dressing 3M Tegasorb™ THIN Hydrocolloid Dressing Product Profile"; 3M Health Care; Form no. 70–2008–3817–8(861)ii; 1996.

*Primary Examiner*—Mickey Yu
*Assistant Examiner*—Tram A. Nguyen
*Attorney, Agent, or Firm*—Eloise J. Maki; Stephen W. Bauer; Kevin W. Raasch

[57] ABSTRACT

Combinations of medical adhesive composites, e.g., dressings, and a package in which the medical adhesive composites are attached to a release surface on the bottom sheet of the package are disclosed. The dressings may include a flexible backing and carrier. Methods of manufacturing and using the combination are also disclosed.

26 Claims, 7 Drawing Sheets

U.S. PATENT DOCUMENTS

| | | | |
|---|---|---|---|
| Re. 33,727 | 10/1991 | Sims | 128/85 |
| 1,949,271 | 2/1934 | Duhamel | 128/268 |
| 2,172,455 | 9/1939 | Samuel | 128/156 |
| 2,402,982 | 7/1946 | Steenbergen | 206/63.2 |
| 2,432,541 | 12/1947 | Peck | 128/156 |
| 2,529,060 | 11/1950 | Trillich | 117/68.5 |
| 2,532,011 | 11/1950 | Dahlquist et al. | 154/53.5 |
| 2,627,341 | 2/1953 | Morgan | 206/63.2 |
| 2,676,702 | 4/1954 | Whitefoot, Jr. | 206/63.2 |
| 2,703,083 | 3/1955 | Gross | 128/156 |
| 2,721,550 | 10/1955 | Banff | 128/156 |
| 2,734,503 | 2/1956 | Doyle | 128/156 |
| 2,752,038 | 6/1956 | Abbott | 206/63.2 |
| 2,806,593 | 9/1957 | Abbott | 206/63.2 |
| 2,836,178 | 5/1958 | Barr | 128/155 |
| 2,840,080 | 6/1958 | Clark | 128/296 |
| 2,880,863 | 4/1959 | Stanton . |  |
| 2,889,039 | 6/1959 | Schladermundt et al. | 206/63.2 |
| 2,924,331 | 2/1960 | Hoey | 206/63.2 |
| 2,927,689 | 3/1960 | Look, Jr. | 206/63.2 |
| 2,946,435 | 7/1960 | Schladermundt et al. | 206/63.2 |
| 2,969,144 | 1/1961 | Zackheim | 206/63.2 |
| 2,969,145 | 1/1961 | Hannauer, Jr. | 206/63.2 |
| 2,973,859 | 3/1961 | Schladermundt et al. | 206/63.2 |
| 3,017,990 | 1/1962 | Singerman | 206/63.2 |
| 3,018,881 | 1/1962 | Wall | 206/56 |
| 3,020,186 | 2/1962 | Lawrence | 156/248 |
| 3,313,405 | 4/1967 | Blackford | 206/63.2 |
| 3,329,548 | 7/1967 | Blatz | 156/251 |
| 3,389,827 | 6/1968 | Abere et al. | 220/53 |
| 3,612,265 | 10/1971 | Dickerson | 206/63.2 |
| 3,645,835 | 2/1972 | Hodgson | 161/146 |
| 3,678,933 | 7/1972 | Moore et al. | 128/296 |
| 3,899,077 | 8/1975 | Spiegelberg | 206/441 |
| 3,900,105 | 8/1975 | Wolfelsperger | 206/498 |
| 4,094,316 | 6/1978 | Nathanson | 128/156 |
| 4,112,213 | 9/1978 | Waldman | 526/279 |
| 4,161,176 | 7/1979 | Harris, II et al. | 128/155 |
| 4,182,449 | 1/1980 | Kozlow | 206/441 |
| 4,264,008 | 4/1981 | Kozlow | 206/441 |
| 4,265,234 | 5/1981 | Schaar | 128/156 |
| 4,281,650 | 8/1981 | Spiegelberg | 128/156 |
| 4,304,333 | 12/1981 | Kozlow, Sr. | 206/441 |
| 4,310,509 | 1/1982 | Berglund et al. | 424/28 |
| 4,323,557 | 4/1982 | Rosso et al. | 424/28 |
| 4,328,057 | 5/1982 | Gutow | 156/248 |
| 4,374,520 | 2/1983 | Grossman et al. | 128/132 |
| 4,413,621 | 11/1983 | McCracken et al. | 128/156 |
| 4,472,480 | 9/1984 | Olson | 428/332 |
| 4,485,809 | 12/1984 | Dellas | 128/156 |
| 4,499,896 | 2/1985 | Heinecke | 128/156 |
| 4,513,739 | 4/1985 | Johns | 128/156 |
| 4,524,095 | 6/1985 | Gockel et al. | 428/43 |
| 4,545,371 | 10/1985 | Grossman et al. | 128/132 |
| 4,549,063 | 10/1985 | Ang et al. | 219/121 |
| 4,549,653 | 10/1985 | Lauritzen | 206/441 |
| 4,561,435 | 12/1985 | McKnight et al. | 128/136 |
| 4,587,146 | 5/1986 | Anhäuser et al. | 428/41 |
| 4,590,022 | 5/1986 | Cloca et al. | 264/41 |
| 4,595,001 | 6/1986 | Potter et al. | 128/156 |
| 4,595,011 | 6/1986 | Phillips | 128/636 |
| 4,596,738 | 6/1986 | Metcalfe et al. | 428/308 |
| 4,598,004 | 7/1986 | Heinecke | 428/40 |
| 4,600,001 | 7/1986 | Gilman | 128/156 |
| 4,614,183 | 9/1986 | McCracken et al. | 128/132 |
| 4,664,106 | 5/1987 | Snedeker | 128/156 |
| 4,669,458 | 6/1987 | Abraham et al. | 128/133 |
| 4,678,462 | 7/1987 | Vaillancourt | 604/180 |
| 4,706,662 | 11/1987 | Thompson | 128/155 |
| 4,733,659 | 3/1988 | Edenbaum et al. | 128/156 |
| 4,737,410 | 4/1988 | Kantner | 428/343 |
| 4,738,257 | 4/1988 | Meyer et al. | 128/156 |
| 4,742,826 | 5/1988 | McLorg | 128/335 |
| 4,743,232 | 5/1988 | Kruger | 604/180 |
| 4,744,355 | 5/1988 | Faasse, Jr. | 128/156 |
| 4,753,232 | 6/1988 | Ward | 128/156 |
| 4,773,409 | 9/1988 | Cilento et al. | 128/156 |
| 4,781,293 | 11/1988 | Johns | 206/441 |
| 4,787,380 | 11/1988 | Scott | 128/156 |
| 4,832,008 | 5/1989 | Gilman | 128/155 |
| 4,884,563 | 12/1989 | Sessions | 128/155 |
| 4,901,714 | 2/1990 | Jensen | 128/156 |
| 4,913,138 | 4/1990 | Yoshida et al. | 128/155 |
| 4,915,227 | 4/1990 | Johns | 206/441 |
| 4,915,228 | 4/1990 | Johns | 206/441 |
| 4,917,112 | 4/1990 | Kalt | 128/156 |
| 4,917,928 | 4/1990 | Heinecke | 428/41 |
| 4,917,929 | 4/1990 | Heinecke | 428/41 |
| 5,012,801 | 5/1991 | Feret | 128/155 |
| 5,018,516 | 5/1991 | Gilman | 128/155 |
| 5,035,687 | 7/1991 | Sandbank | 604/180 |
| 5,052,381 | 10/1991 | Gilbert et al. | 128/155 |
| 5,061,258 | 10/1991 | Martz | 604/307 |
| 5,086,764 | 2/1992 | Gilman | 602/42 |
| 5,088,483 | 2/1992 | Heinecke | 602/46 |
| 5,099,832 | 3/1992 | Ward | 602/57 |
| 5,106,383 | 4/1992 | Mulder et al. | 604/389 |
| 5,106,629 | 4/1992 | Cartmell et al. | 424/445 |
| 5,123,900 | 6/1992 | Wick | 602/41 |
| 5,153,040 | 10/1992 | Faasse, Jr. | 428/40 |
| 5,158,555 | 10/1992 | Porzilli | 604/307 |
| 5,160,315 | 11/1992 | Heinecke et al. | 602/57 |
| 5,188,124 | 2/1993 | Feret | 128/889 |
| 5,230,350 | 7/1993 | Fentress | 128/846 |
| 5,254,109 | 10/1993 | Smith et al. | 604/289 |
| 5,264,281 | 11/1993 | Arakawa et al. | 428/354 |
| 5,275,284 | 1/1994 | Onotsky | 206/441 |
| 5,277,954 | 1/1994 | Carpenter et al. | 428/71 |
| 5,336,162 | 8/1994 | Ota et al. | 602/41 |
| 5,344,415 | 9/1994 | DeBusk et al. | 604/304 |
| 5,370,924 | 12/1994 | Kochinke | 428/224 |
| 5,413,567 | 5/1995 | Barth et al. | 604/307 |
| 5,415,627 | 5/1995 | Rasmussen et al. | 602/57 |
| 5,423,737 | 6/1995 | Cartmell et al. | 602/57 |
| 5,511,689 | 4/1996 | Frank | 221/73 |
| 5,520,629 | 5/1996 | Heinecke et al. | 602/57 |
| 5,531,855 | 7/1996 | Heinecke et al. | 156/252 |
| 5,628,724 | 5/1997 | DeBusk et al. | 602/58 |
| 5,662,925 | 9/1997 | Ebert et al. | 424/447 |
| 5,722,943 | 3/1998 | Sessions | 602/57 |
| 5,738,642 | 4/1998 | Heinecke et al. | 602/58 |

FOREIGN PATENT DOCUMENTS

| | | | |
|---|---|---|---|
| 0 541 251 | 5/1993 | European Pat. Off. | A61F 13/02 |
| 0 437 944 B1 | 8/1994 | European Pat. Off. . |  |
| 59-214449 | 12/1984 | Japan | A61F 13/02 |
| 2 120 104 | 11/1983 | United Kingdom | A61F 13/00 |
| 2 131 299 | 6/1984 | United Kingdom | A61F 13/02 |
| WO 94/21207 | 9/1994 | WIPO . |  |
| WO 95/18046 | 7/1995 | WIPO | B65D 1/09 |

MEDICAL ADHESIVE COMPOSITE AND PACKAGE

RELATED APPLICATIONS

This is a continuation-in-part of U.S. application Ser. No. 08/677,426 filed on Jul. 2, 1996, now abandoned, which is hereby incorporated by reference in its entirety.

FIELD OF THE INVENTION

The present invention relates to a combination of a package and a medical adhesive composite such as a dressing. The present invention also relates to methods of manufacturing and using the combination.

BACKGROUND OF THE INVENTION

Articles coated with pressure sensitive adhesive find many uses in the medical and surgical products area. Examples of medical adhesive composites include bandages, dressings, drapes, electrodes, etc. These items are typically packaged to prevent contamination and, in some cases, maintain their sterility until the package in which the medical adhesive composites are located. The packaging must also typically allow for sterilization after the medical adhesive composites have been packaged.

Among the products that are considered medical adhesive composites are polymeric film dressings. These dressings are widely used as protective layers over wounds because they facilitate healing in a moist environment while acting as a barrier to contaminating liquids and bacteria. The polymeric films are also used as surgical drapes because of their barrier properties. Dressings and drapes fitting the above description are available under a number of trade names such as TEGADERM™ (3M Company, St. Paul, Minn.), BIOCLUSIVE™ (Johnson & Johnson Company, New Brunswick, N.J.), OP-SITE™ (T. J. Smith & Nephew, Hull, England), and UNIFLEX™ (How Medica, Largo, Fla.).

The polymeric films used in those dressings are conformable, i.e., the films are extremely thin, flexible and supple and usually transparent. They are typically supplied with a releasable protective liner covering the adhesive coated surface of the film. When the liner is removed, the adhesive coated film tends to wrinkle and adhere to itself, interfering with the smooth, aseptic application of the dressing to a patient's skin. Various delivery systems have been proposed to address this problem.

A number of the delivery systems rely on a carrier frame to prevent wrinkling of the film before application to a patient's skin by providing a more rigid construction. The frame can then typically be removed after the dressing is in place. Examples of some frame-delivered thin film dressings are described in U.S. Pat. No. 5,531,855 issued Jul. 2, 1996, titled CARRIER DELIVERED DRESSING AND METHOD OF MANUFACTURE; EPO Publication No. 0 051 935; U.S. Pat. No. Re 33,727.

A number of these delivery systems include a liner to protect the adhesive on the thin film dressing before application to the patient. In use, the liner should be removed to expose the adhesive that attaches the dressing to a patient before the carrier is removed from the dressing. The carrier is removed when the dressing is in place on the patient. Some users may remove the carrier before the liner which can cause the dressing to fold onto itself in part or total. As a result there is a need for an adhesive composite dressing and packaging system that facilitates rapid, uniform application of thin film dressings onto a patient.

SUMMARY OF THE INVENTION

The present invention provides the combination of medical adhesive composites, e.g., dressings, in a package. The medical adhesive composites include pressure sensitive adhesives that are attached to a release surface located on a bottom sheet of the packaging material. By adhering the medical adhesive composites directly to the bottom sheet of the packaging material rather than including a separate release liner on the product simplifies the process of dispensing the medical adhesive composites.

In one aspect, the present invention provides medical adhesive composite dressings including a backing having top and bottom faces, a pressure sensitive adhesive coated on at least a portion of the bottom face of the backing, and a carrier attached to the backing and formed of material substantially more rigid than the backing, the carrier supporting the backing. The dressings are provided in combination with a package including a top sheet located over the top face of the backing and the carrier and a bottom sheet located under the adhesive on the bottom face of the backing, wherein the composite dressing is located between the top and bottom sheets, and further wherein the top and bottom sheets are sealed to each other about the periphery of the dressing. The bottom sheet includes a release surface at least as large as the pressure sensitive adhesive on the bottom face of the backing, the release surface attached to the bottom sheet, wherein the bond strength between the release surface and the bottom sheet is greater than the bond strength between the release surface and the adhesive on the bottom face of the dressing. The release surface can be provided as a coating on the bottom sheet or as a coating on a separate release liner attached to the bottom sheet.

The present invention also provides methods for making a combination of an adhesive composite dressing in a package including the steps of providing a composite dressing including a backing having top and bottom faces and a pressure sensitive adhesive on the bottom face of the backing; attaching a carrier to the top face of the backing, the carrier supporting the backing; providing a bottom sheet of packaging material; providing a release surface between the bottom sheet of packaging material and the adhesive on the bottom face of the backing, wherein the bond between the release surface and the bottom sheet is stronger than the bond between the release surface and the adhesive; providing a top sheet of packaging material over the composite dressing wherein the composite dressing is located between the top and bottom sheets; and sealing the top sheet to the bottom sheet about the periphery of the composite dressing. The release surface can be provided as a coating on the bottom sheet or as a coating on a separate release liner attached to the bottom sheet.

The present invention provides methods of using a combination adhesive composite dressing and package including the step of providing a combination dressing and package. The adhesive composite dressing includes a backing having top and bottom faces, a pressure sensitive adhesive coated on at least a portion of the bottom face of the backing, a carrier attached to the backing and formed of material substantially more rigid than the backing, the carrier supporting the backing. The package housing the composite dressing includes a top sheet located over the top face of the backing and the carrier, a bottom sheet located under the adhesive on the bottom face of the backing, wherein the composite dressing is located between the top and bottom sheets, and further wherein the top and bottom sheets are sealed to each other about the periphery of the dressing; and a release surface at least as large as the pressure sensitive adhesive, the release surface attached to the bottom sheet, wherein the bond strength between the release surface and the bottom sheet is greater than the bond strength between the release surface and the adhesive on the bottom face of the dressing. After the combination is provided, method includes separating at least a portion of the top sheet from the bottom sheet to expose the adhesive composite dressing; separating the adhesive on the bottom face of the backing from the release surface, wherein the adhesive composite dressing is removed from the bottom sheet of the packaging material; applying the adhesive and attached backing to a patient. The release surface can be provided as a coating on the bottom sheet or as a coating on a separate release liner attached to the bottom sheet.

The present invention also provides combination of a medical adhesive composite in a package. The medical adhesive composite includes a substrate having top and bottom faces; a pressure sensitive adhesive coated on at least a portion of the bottom face of the substrate. The accompanying package housing the medical adhesive composite includes a top sheet located over the top face of the substrate of the medical adhesive composite; a bottom sheet located under the adhesive on the medical adhesive composite, wherein the medical adhesive composite is located between the top and bottom sheets, and further wherein the top and bottom sheets are sealed to each other about the periphery of the medical adhesive composite; and release surface at least as large as the pressure sensitive adhesive on the bottom face of the backing, the release surface comprising a release liner attached to the bottom sheet, wherein the bond strength between the release liner and the bottom sheet is greater than the bond strength between the release liner and the adhesive on the medical adhesive composite.

The present invention also provides the combination of a medical adhesive composite in a package. The medical adhesive composite includes a substrate having top and bottom faces; and a pressure sensitive adhesive coated on at least a portion of the bottom face of the substrate. The package of the combination that houses the medical adhesive composite includes a top sheet located over the top face of the substrate of the medical adhesive composite; a bottom sheet located under the adhesive on the medical adhesive composite; cohesive material on at least a portion of the top sheet and over substantially all of the bottom sheet, the cohesive material on the top sheet being opposed to and facing cohesive material on the bottom sheet, wherein the top and bottom sheets are sealed to each other about the periphery of the medical adhesive composite by the cohesive material; and a release surface at least as large as the pressure sensitive adhesive on the medical adhesive composite, the release surface comprising a release coating applied over the cohesive material on the bottom sheet, wherein the bond strength between the release coating and the cohesive material on the bottom sheet is greater than the bond strength between the release coating and the adhesive on the medical adhesive composite.

These and other features and advantages of the combination and methods according to the present invention are set forth in the detailed description and figures presented below.

DETAILED DESCRIPTION OF THE PREFERRED EMBODIMENTS

Figure 1:
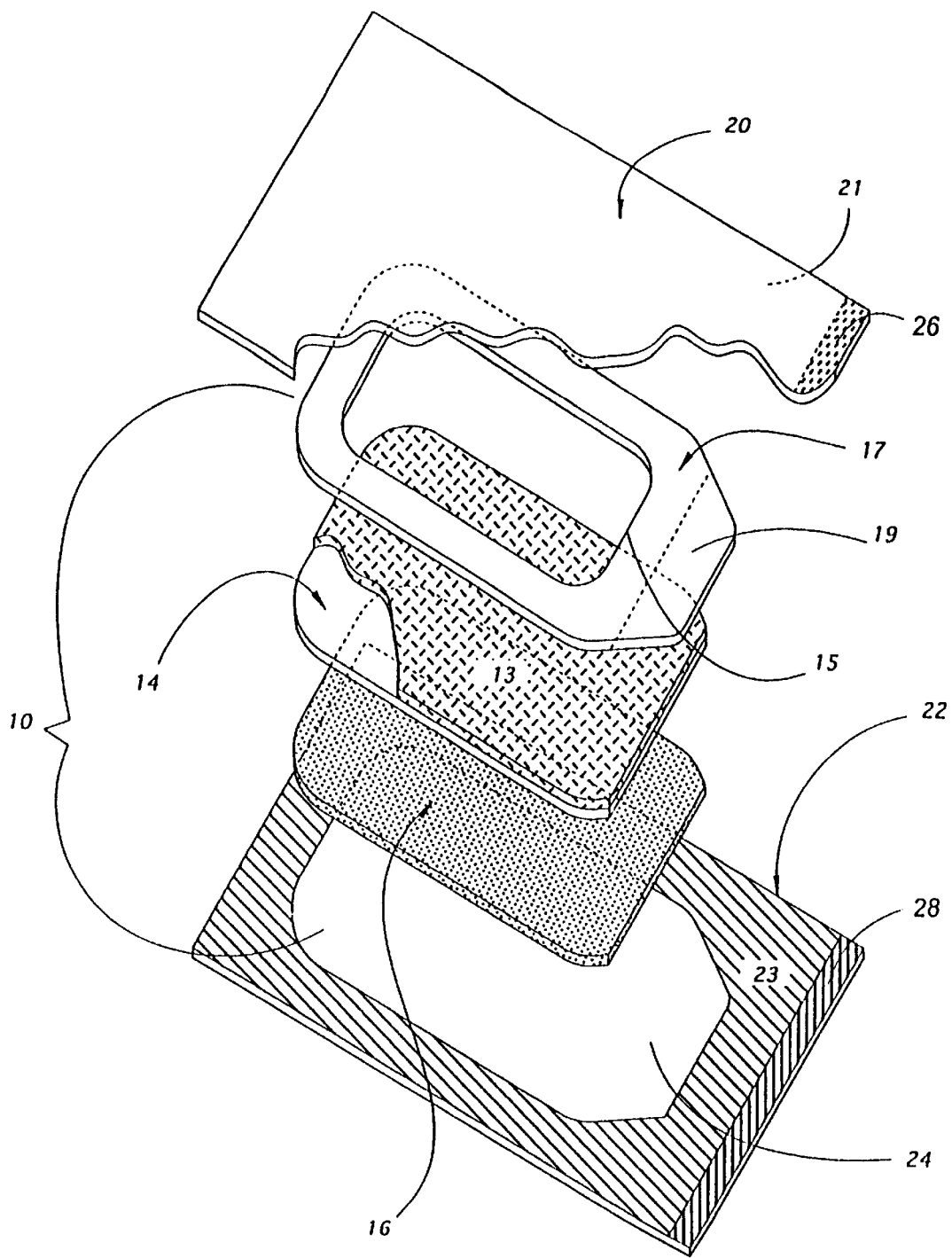
FIG. 1 is an exploded perspective view of one dressing and package combination according to the present invention.

FIG. 1 depicts one example of a adhesive composite product and package combination according to the present invention. The combination of the present invention is useful in connection with any pressure sensitive adhesive coated medical or surgical product that is packaged to prevent contamination and/or maintain product sterility after sterilization. Because the pressure sensitive adhesive coated products used in connection with the present invention typically include a layer of pressure sensitive adhesive on a backing or other substrate, they may be referred to herein as "medical adhesive composites."

Examples of one type of medical adhesive composites useful in connection with the present invention include bandages, dressings, etc. that typically include a flexible backing having a pressure-sensitive adhesive coating positioned on the backing surface. Representative backings include nonwoven fibrous webs, woven fibrous webs, knits, foams, films and other suitable backing materials. The medical adhesive composites may also include electrodes and other devices including a pressure sensitive adhesive layer on a substrate.

Some preferred flexible backing materials for dressings provided in connection with the present invention are translucent or transparent polymeric films, including flexible elastomeric films. The invention is particularly useful in the field of medical adhesive composites having high moisture vapor permeable film backings typically used for dressings, bandages and similar products. Issued U.S. Pat. Nos. 3,645,835 and 4,595,001 describe methods of making such films and methods for testing their permeability. Preferably, the film/adhesive composite should transmit moisture vapor at a rate equal to or greater than human skin. Preferably, the adhesive coated film transmits moisture vapor at a rate of at least 300 g/m$^2$/24 hrs/37/C/100–10% RH, more preferably at least 700 g/m$^2$/24 hrs/37/C/100–10% RH, and most preferably at least 2000 g/m$^2$/24 hrs/37/C/100–10% RH using the inverted cup method as described in U.S. Pat. No. 4,595,001.

The film backings used in connection with the present invention may be conformable to anatomical surfaces. As such, when the film backing is applied to an anatomical surface, it conforms to the surface even when the surface is moved. The preferred film backing is also conformable to anatomical joints. When the joint is flexed and then returned to its unflexed position, the film backing stretches to accommodate the flexion of the joint, but is resilient enough to continue to conform to the joint when the joint is returned to its unflexed condition.

A description of this characteristic of film backings preferred for use with the present invention can be found in issued U.S. Pat. Nos. 5,088,483 and 5,160,315. As discussed, particularly preferred film backings are elastomeric polyurethane, polyester, or polyether block amide films, or combinations thereof. These films combine the desirable properties of resiliency, high moisture vapor permeability, and transparency found in preferred backings.

The pressure sensitive adhesives which can be used in the medical adhesive composites of the present invention are the normal adhesives which are applied to the skin such as the acrylate copolymers described in U.S. Pat. No. RE 24,906, the disclosure of which is hereby incorporated by reference, particularly a 97:3 iso-octyl acrylate:acrylamide copolymer. Also preferred is an 70:15:15 isooctyl acrylate:ethyleneoxide acrylate:acrylic acid terpolymer, as described in U.S. Pat. No. 4,737,410 (see Example 31). Other useful adhesives are described in U.S. Pat. Nos. 3,389,827, 4,112,213, 4,310,509, and 4,323,557. Inclusion of medicaments or antimicrobial agents in the adhesive is also contemplated, as described in U.S. Pat. Nos. 4,310,509 and 4,323,557.

The preferred pressure sensitive adhesives described above preferably transmit moisture vapor at a rate greater to or equal to that of human skin. While such a characteristic can be achieved through the selection of an appropriate adhesive, it is also contemplated in the present invention that other methods of achieving a high relative rate of moisture vapor transmission may be used, such as pattern coating the adhesive on the backing, as described in U.S. Pat. No. 4,595,001.

In the preferred embodiments according to the present invention, the choice of adhesives is limited to those that are safe to use on human or animal skin, and preferably to those that are of the class known as "hypoallergenic" adhesives. The preferred acrylate copolymers are adhesives of this class. Liners are available from a variety of manufacturers in a wide variety of proprietary formulations. Those skilled in the art will normally test those liners in simulated use conditions against an adhesive of choice to arrive at a product with the desired release characteristics.

The carrier material is preferably substantially more rigid than the backing to prevent the backing from wrinkling or folding onto itself in whole of in part during application of the dressing. The carrier material should be capable of being attached to the backing by any suitable method, such as heat sealing, adhesives, mechanical bonds, wax coatings, surface energy attraction, etc. The bond should be secure, yet releasable, i.e., the carrier and backing can be separated without destroying the integrity of the backing or the bond between the pressure sensitive adhesive on the backing and the skin of a patient. That is, the bond strength between the carrier and the backing is less than the bond strength between the adhesive on the backing and the skin of a patient. In addition, the bond between the carrier and the backing should be stronger than the bond between the adhesive on the bottom face of the backing, such as a pressure sensitive adhesive, and the release liner or surface of the packaging as discussed more completely below.

In one preferred embodiment, the carrier material is heat-sealable to the backing, with or without the low adhesion coating described below, for the purpose of manufacturing the preferred dressings. In general, heat-sealable carrier materials can include, but are not limited to, polyethylene/vinyl acetate copolymer-coated papers and polyester films. One example of a preferred heat-sealable carrier material is a polyethylene/vinyl acetate copolymer-coated super calendared Kraft paper (1-80BKG-157 PE; Daubert Coated Products, Inc. Willowbrook, Ill.).

The adhesive composites of the present invention may also include a low adhesion coating on a top face of the backing, which is preferably coated as a solution of polyvinyl N-octadecyl carbamate and a blend of silicone resins, as described in U.S. Pat. No. 5,531,855. The preferred low adhesion coating is compatible with the heat seal bond between the carrier and the backing and also retains its low adhesion characteristics after attachment. While it is preferred that the top face of the adhesive composites of the present invention include a low adhesion coating, adhesive composites without such a coating are also considered to be within the scope of the present invention.

Turning to FIG. 1, one embodiment of a medical adhesive composite dressing 10 comprises a backing 14 which is preferably conformable as described above; a low adhesion coating 13 on a top face of the backing 14; a carrier 17 attached to the top face of the backing 14 over the low adhesion coating 13; and a pressure-sensitive adhesive 16 on a bottom face of the backing 14. It will be understood that the low adhesion coating is optional in dressings 10.

In FIG. 1, a window portion cut in the carrier 17 is preferably removed creating a window 15 exposing a portion of the top face of the backing 14. The window 15 is useful to assist in placement of the dressing 10 on a patient when the backing 14 is transparent or semi-transparent. It will be understood, however, that in some instances the carrier 17 may not include a window 15, i.e., the carrier 17 may be coextensive with the backing 14.

In those dressings 10 in which a window is provided, removal of the window portion of the carrier material 17 which would normally cover window 15 is optional during manufacture. Removal does eliminate one step in the delivery process for previously known window style dressings (i.e., the step of removing a portion of the carrier material from the window 15 prior to removing the dressing 10 from the bottom sheet 22) and reduces the waste stream at the consumer level. However, some customers prefer that the portion of the carrier 17 normally covering window 15 remain intact until the dressing 10 reaches the end user. The portion of the carrier 17 that remains after window removal preferably forms a frame about a substantial portion of the periphery of the backing 14 to support it after removal from the package.

Carrier 17 preferably includes at least one tab 19 that extends beyond the perimeter of backing 14 to provide a means of removing the dressing 10 from the bottom sheet 22 of the packaging without contacting the adhesive 16. It is preferred that the tab 19 be completely integral with the carrier 17 such that pulling it away from the bottom sheet 22 of packaging material (described below) results in removal of the dressing 10 from the packaging material.

The carrier 17 is preferably attached to backing 14 (over low adhesion coating 13) with a heat seal bond. Other bonding mechanisms, such as adhesives, mechanical bonds, wax coatings, surface energy attraction, etc. can be used in place of the preferred heat seal bond. Regardless of the type of bonding used to attach the carrier 17 to the backing 14, the bond should be secure, yet releasable, i.e., the carrier 17 and backing 14 can be separated without destroying the integrity of the backing 14 or the bond between the pressure sensitive adhesive 16 on the backing and the skin of a patient after application of the dressing.

The dressing 10 is located in a package having a top sheet 20 and bottom sheet 22. The materials used for the packaging sheets 20 and 22 can be papers, polyethylene, polypropylene, polyester or composites of any of these materials. The primary requirements for the packaging materials are the ability to provide a sealable package and compatibility with sterilization processes. One preferred packaging material for the top and bottom sheets 20 and 22 is a 25 pound Rhinelander Medical Kraft Paper (Phoenix Products Company, Inc., Milwaukee, Wis.)

The top sheet 20 and bottom sheet 22 each preferably include a layer 21 and 23, respectively, of cohesive material on their respective facing or inner surfaces. The cohesive material forms a bond when activated, typically through pressure or pressure and heat. One example of a suitable cohesive material is described in U.S. Pat. No. 2,529,060. As a result, the areas of the top sheet 20 and bottom sheet 22 that are not separated by the dressing 10 are bonded together to seal the dressing 10 in between the top and bottom sheets 20 and 22 of the package.

Although one preferred means of bonding the top and bottom sheets 20 and 22 of packaging material is cohesive material as described above, it will be understood that the top and bottom sheets 20 and 22 of packaging material could be sealed around each dressing 10 by any other suitable means including heat sealing, contact adhesives, pressure sensitive adhesives, mechanical bonds, etc. Regardless of the sealing mechanism, it is preferred that it be compatible with sterilization process, e.g., gamma irradiation, ethylene oxide, etc.

It is preferred that one or both of the top sheet 20 and bottom sheet 22 be unattached along one edge to form tabs 26 and 28 that are not bonded together. Tabs 26 and 28 facilitate separation of the top and bottom sheets 20 and 22 to expose the dressing 10 for removal from the bottom sheet 22.

The bottom sheet 22 preferably includes a release surface 24 on which the adhesive 16 of the backing 14 lies when the combination dressing and package is manufactured. The release surface 24 should be at least as large as the adhesive 16 on the backing 14, but may in some instances be larger to simplify attachment and placement of the dressing 10 on the bottom sheet 22 of the packaging material.

Figure 1A:
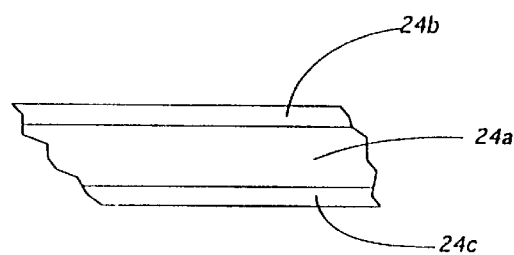
FIG. 1A is an enlarged partial cross-sectional view of a release surface useful in some combinations according to the present invention.

The release surface 24 can comprise a release coating on the surface of the bottom sheet 22 or, referring to FIG. 1A, release surface 24 can be provided in the form of a separate liner 24a which is itself coated with a release coating 24b. The liner 24a can then be separately attached to the bottom sheet 22 of packaging material with the release surface 24b exposed to bond with the adhesive 16 on the dressing 10. Except as otherwise indicated, the term "release surface" will be used below to describe either a release coating provided on the bottom sheet 22 or a release agent 24b provided on a liner 24a attached to the bottom sheet 22.

In those embodiments in which the release surface 24 is a release coating applied to the bottom sheet 22, it will be understood that the adhesive used to seal the top and bottom sheets 20 and 22 of packaging material could be applied over the entire surface of the bottom sheet 22. If the adhesive 23 is provided on the entire surface of the bottom sheet 22, the release surface 24 could be provided by coating a layer of a release material, e.g., a 100% solids ultraviolet curable silicone release material, directly on the adhesive 23 located on the bottom sheet 22. Examples of suitable release materials include silicones such as UV-9300 and UV-9315 available from GE Silicones, General Electric Company, Waterford, N.Y.

The release material making up release surface 24 would preferably be coated at weights sufficient to provide the desired release characteristics to allow removal of the backing 13 when desired. For the exemplary release materials described above, the coating weights will typically be about 0.6 grams per square meter or more, more preferably about 0.9 grams per square meter or more. Typically the release materials will be coated at no more than about 5 grams per square meter, more preferably no more than about 2.0 grams per square meter.

The release coating 24 could be applied, for example, by off-set printing, rotary screen printing, rotogravure processes and any other equivalent method or methods known to those of skill in the art.

Release liners 24a that are suitable for use as the release surface 24 in the combination of the present invention can be made of kraft papers, polyethylene, polypropylene, polyester or composites of any of these materials. As discussed above, the release surface 24 preferably comprises release agents such as fluorochemicals or silicones. For example, U.S. Pat. No. 4,472,480, the disclosure of which is hereby incorporated by reference, describes low surface energy perfluorochemical liners. Some preferred liners are papers, polyolefin films, or polyester films coated with silicone release materials. Examples of commercially available silicone coated release papers are POLYSLIK™ silicone release papers available from James River Co., H. P. Smith Division (Bedford Park, Ill.) and silicone release papers supplied by Daubert Coated Products, Inc. (Willowbrook, Ill.). Some preferred liners are described in the examples below.

Other combinations of adhesives and release agents are contemplated for use with embodiments according to the present invention. Those skilled in the art will be familiar with the processes of testing new combinations of adhesives and release surfaces to arrive at the combination of qualities desired in a final product. The considerations pertinent to the selection of silicone release surfaces can be found in Chapter 18 of the *Handbook of Pressure Sensitive Adhesive Technology*, Van Nostrand-Reinhold, 1982, pp. 384–403. U.S. Pat. No. 4,472,480 also describes considerations pertinent to the selection of a perfluoropolyether release liner.

Where the release surface 24 is provided on a separate release liner (as shown in FIG. 1A) the release liner 24a is preferably attached to the bottom sheet 22 using the same cohesive material used to bond the top and bottom sheets 20 and 22 of packaging material together. As a result, the release liner 24a includes a layer 24c of the cohesive material on its bottom surface, i.e., the surface facing the bottom sheet 22 of the package (see FIG. 1). That layer 24c of cohesive material bonds to the layer 23 of cohesive material on the bottom sheet 22 of the package. As a result, the dressing 10 can be secured in place on the bottom sheet 22 at the same time the top and bottom sheets 20 and 22 are bonded to each other. Alternatively, the release liner 24a can be bonded to the bottom sheet 22 by any suitable means including, but not limited to: contact adhesives, pressure sensitive adhesives, mechanical bonds, heat sealing, wax coatings, surface energy attraction, etc.

One potential advantage for those systems using separate release liners 24a to provide the release surface 24 is that it may be easier to prevent wrinkling or other deformation of the dressing 10 during placement between packaging sheets 20 and 22. As described above, the preferred dressings 10 employ a highly conformable, flexible backing 14 that has a tendency to fold onto itself. Although the carrier 17 can assist in preventing wrinkling of the backing 14, the addition of release liner 24a to the composite dressing 10 can further assist in preventing wrinkles form occurring during packaging of the dressings 10.

Regardless of the actual mechanism used to provide a release surface 24 on the bottom sheet 22 of packaging material, the bond between the release surface 24 and the bottom sheet 22 of the package material should be stronger than the bond between the adhesive 16 of dressing 10 and the release surface 24 to ensure easy and consistent removal of the dressing 10 from the bottom sheet 22 of the package. It is that difference in relative bond strengths that provides the easy to use combination of the present invention.

Also, regardless of whether the release surface 24 is provided by coating a release material on the adhesive layer 23 on bottom sheet 22 or whether a release liner 24a is attached to the bottom sheet 22, the present invention can provide a significant advantage by reducing packaging material inventory requirements. Inventory can be reduced because only one type of packaging material used for the bottom sheets 22 of the packages is required because the desired release surface 24 of the appropriate size can be supplied in line with the packaging of the dressings. This concept will be discussed in more detail below with reference to FIGS. 8 and 9.

Figure 3A:
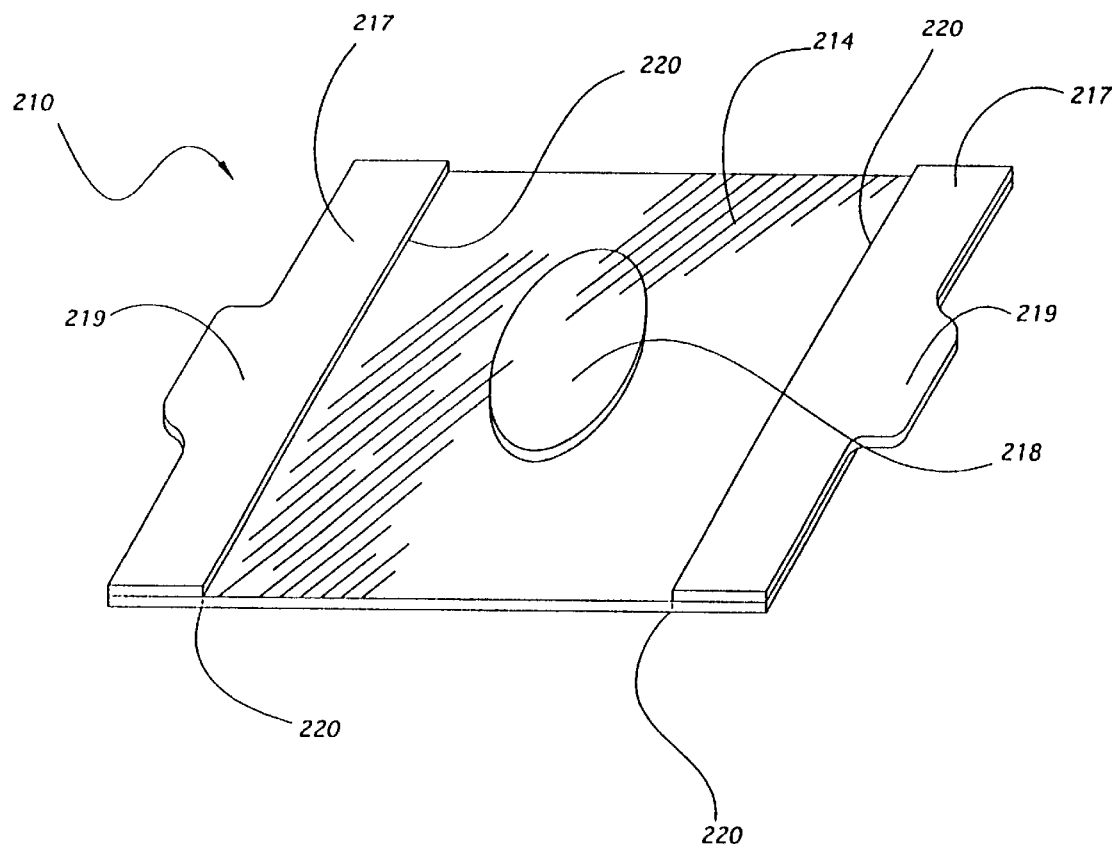
FIG. 3A is a top perspective view of an alternative dressing for use in the combination according to the present invention.
Figure 2:
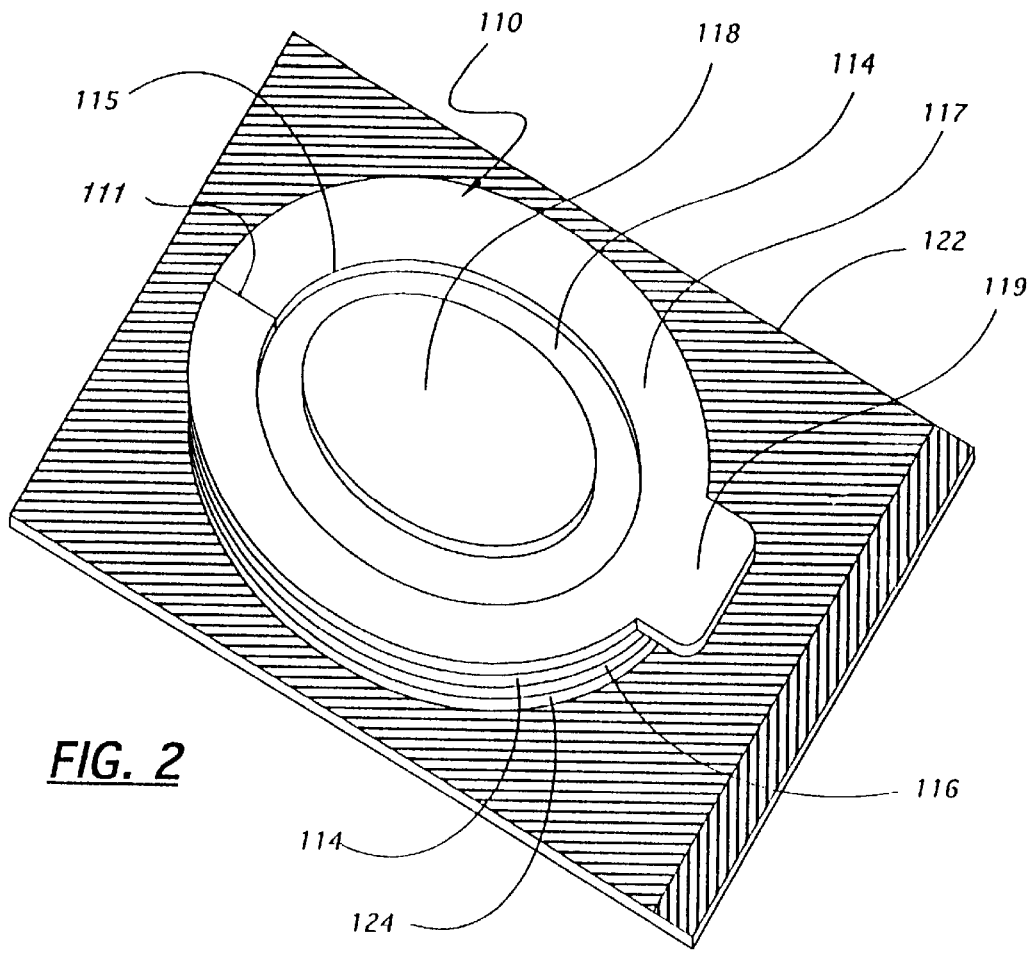
FIG. 2 is a top perspective view of an alternative dressing attached to the bottom sheet of the package in one combination according to the present invention.
Figure 3:
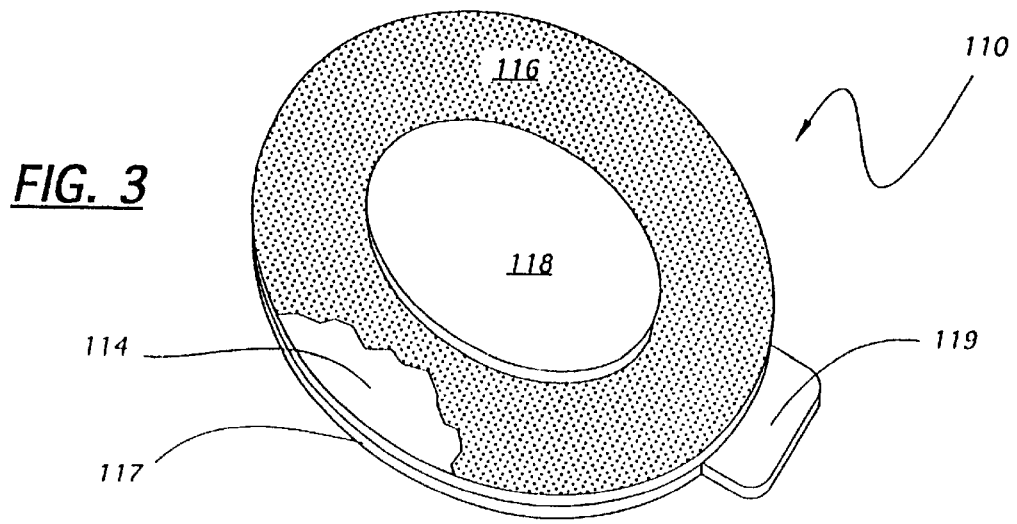
FIG. 3 is a bottom perspective view of the dressing of FIG. 2 after removal from the bottom sheet of the package.

An alternate embodiment of a dressing 110 for use with a package according to the present invention is depicted in FIGS. 2 and 3. The dressing 110 is an adhesive composite comprising a carrier 117, a backing 114, pressure-sensitive adhesive 116, and a pad 118 attached to the adhesive 116. The backing 114 has top and bottom faces. The dressing 110 is located on the bottom sheet 122 of a package in a manner similar to that described for dressing 10 above.

Carrier 117 preferably has at least one tab 119 for handling the dressing 110. As with dressing 10 in FIG. 1, dressing 110 also includes an open area or window 115 which exposes a portion of the top surface of backing 114. The carrier 117 preferably extends around the entire perimeter of backing 114 and may include a control depth die cut 111 to facilitate removal of the carrier 117 from backing 114 after the dressing 110 has been applied to a patient.

FIG. 3 is a bottom view of dressing 110 depicting the exposed adhesive layer 116 and pad 118 disposed proximate the center of the dressing 110. Pad 118, which is typically absorbent, can be manufactured from a number of materials including, but not limited to, woven or nonwoven cotton, rayon, nonwovens, hydrocolloids, foams, and combinations thereof. Pad 118 may also contain a number of substances, including antimicrobial agents, drugs for transdermal drug delivery, chemical indicators to monitor hormones or other substances in a patient, combinations thereof, and the like. Furthermore, although pad 118 is shown as centered on dressing 110, it can take any appropriate shape and/or can be located off-center on the dressing 110 as desired.

It should be noted that the removal by the manufacturer of the carrier material 117 from the window area 115 of dressing 110 is advantageous in dressings incorporating a pad 118. The pad 118 tends to deform the backing 114 and cause delamination between the carrier material 117 that would normally be located in the window 115 if that material is still present when pad 118 is placed on dressing 110.

In addition, the use of a separate release liner to provide the desired release surface 124 on bottom sheet 122 of the package can also assist in supporting the backing 114 during placement of the dressing 110 between package top and bottom sheets 120 and 122. This advantage may be especially helpful when using dressings in which a portion of the backing is unsupported by a carrier.

As shown in FIGS. 1–3, the carrier is provided to support the backing after removal from the package. As used in connection with the present invention, the term "support" is used to indicate that the carrier allows a user to hold the backing in any desired orientation after removal of the dressing from the bottom sheet of the package while preventing the backing from wrinkling or folding upon itself. It is preferred that the carrier support all or at least a substantial portion of the periphery of the backing by being releasably attached to a the entire surface of the backing or at least a substantial portion of that periphery. It may, however, be sufficient to support two opposing sides of the backing as depicted in FIG. 3A. There the carrier 217 includes two separate pieces attached to the same backing 214 in an opposing arrangement. Each portion of the carrier 217 preferably includes a tab 219 to facilitate handling of the dressing 210. After the dressing 210 is removed from the package (not shown) the backing 214 can be held in tension using the opposing carrier portions 217 to allow the dressing to be applied without wrinkling after which the carrier portions 217 can be removed.

The addition of a pad 218 on the dressing 210 can also assist in supporting the backing 214 by separately supporting the backing 214 in the area of the pad 218 after removal of the dressing 210 from the package.

The carrier portions 217 can be removed from the backing as described with dressings above. Alternatively, dressing 210 can also include a different bond between the carrier 217 and backing 214 in which the carrier is more securely attached to the backing 214. In that variation, the backing 214 is preferably perforated along the edges 220 of the carrier portions 217 to facilitate removal of the carrier 217 (and attached backing 214) after the dressing 210 has been applied to a patient.

Although FIGS. 1–3A depict dressings useful in the combination according to the present invention, it should be understood that the dressings can take on any desired shape. In addition, the dressings could incorporate additional features such as windows for allergy testing, reservoirs to collect drainage fluids, etc.

Figure 4:
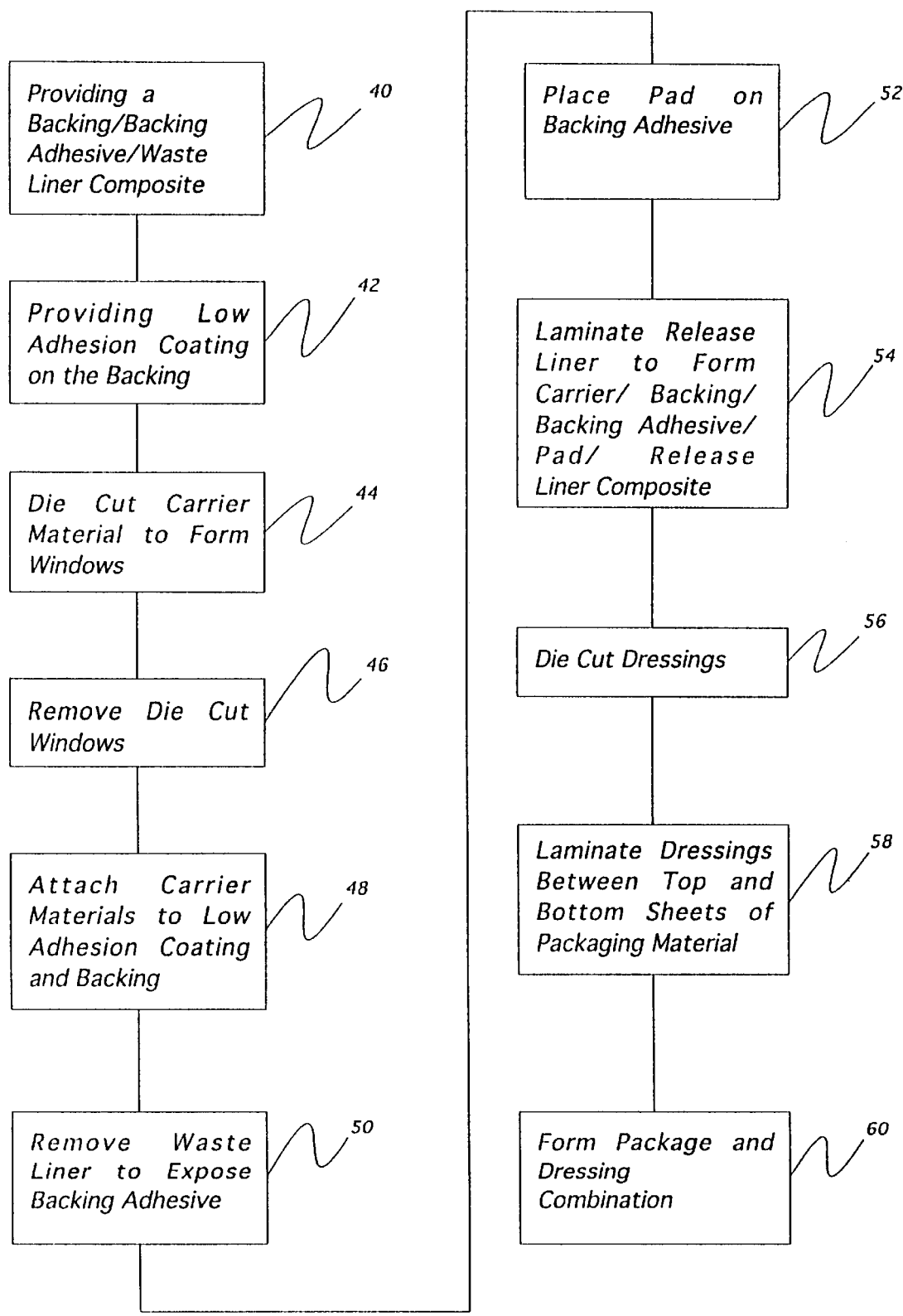
FIG. 4 is a flow chart depicting the steps in one method of manufacturing the dressing and package combination according to the present invention.

Turning now to FIGS. 4–9, flowcharts and schematic diagrams depicting some methods of manufacturing the combination of dressings in a package according to the present invention will be described. Referring to FIG. 4, step 40 preferably comprises providing an adhesive composite formed of a backing/backing (pressure sensitive) adhesive/waste liner. Some preferred materials for the backing and backing adhesive are described above. The waste liner preferably comprises any suitable liner having release characteristics to allow for easy removal from the backing adhesive as discussed below.

Step 42 comprises providing a low adhesion coating on the top face of the backing as described in U.S. Pat. No. 5,531,855 to provide a tape-over feature, as well as to minimize surface friction between the backing and other objects or surfaces which also reduces unwanted removal of the dressings. It will be understood that this step is optional and that the low adhesion coating may or may not be provided.

The carrier material is die cut 44 to form the windows which lie in the center of the carriers on some dressings provided in the combinations according to the present invention. The die cutting can be accomplished using rotary die cutting equipment which is well known to those skilled in the art. After the windows have been die cut in the carrier material, they are optionally removed in step 46 before the carrier material is attached to the adhesive composite. The windows die cut into the carrier material can be removed using a number of methods known to those skilled in the art. Those methods could include the use of vacuum, air pressure, gravity, and/or small diameter nip rolls that cause the windows to be removed from the framed carrier material. It will be understood that although steps 42, 44 and 46 are depicted sequentially in FIG. 4, they could be performed simultaneously and are shown sequentially only for convenience.

Although one preferred method comprises providing windows in the carrier material, it will be understood that the carrier may not include any windows in which case the carrier will typically be attached over the entire top surface of the backing.

After the optional low adhesion coating 42, die cutting 44 and window removal steps 46 are completed, the carrier material (with windows removed) can be attached 48 to the top face of the backing, over the low adhesion coating. The attaching step 48 can include heat sealing, adhesive attachment, mechanical bonding, wax coatings, surface energy attraction, etc. provided a suitable bond between the carrier and backing is provided. As discussed above, it is desirable for the present invention that the bond between the carrier and the backing be stronger than the bond between the release surface on the bottom sheet of the package and the adhesive coated on the backing.

Although the window die cutting and removal steps 44 and 46 are depicted as occurring before attaching the carrier to the backing in step 48, an alternate preferred method involves attaching the carrier to the backing in step 48 before the die cutting and window removal steps 44 and 46. In that method, the carrier is preferably not attached to the backing in the optional window areas to ease removal of the windows from the composite dressing. In addition, the die cutting step 44 now involves control depth die cutting of the carrier material to avoid cutting through the backing when the windows are cut out of the carrier material.

After the windows have been removed in steps 44 and 46 and the attaching step 48 has been performed, the waste liner used to protect the backing adhesive on the backing is removed in step 50 to expose the backing adhesive. The remaining composite of carrier/backing/backing adhesive is then passed through a nip station at which time a pad can be placed on the backing adhesive in step 52. The pad is preferably placed in step 52 using a die cut roll that cuts the pad into the desired shape from a web of pad material (described above) and places the pad on the backing adhesive. Alternative methods of providing a pad will be known to those skilled in the art and include, for example, pick-and-place equipment or any other suitable method. Also, it will be understood that the dressings may be constructed without any pad and, therefore, that step 52 is optional.

After the pad is placed in step 52, the composite dressing, now comprising a carrier/backing/backing adhesive/pad is laminated to a release liner in step 54, typically using a set of nip rolls. The release liner preferably includes the cohesive material needed to attach the release liner (and its attached dressing) to the bottom sheet of the package as discussed above. The cohesive material is provided on the side of the release liner that is opposite the surface laminated to the backing adhesive.

The result of step 54 is a laminate comprising the carrier/low adhesion coating/backing/backing adhesive/pad/release liner/cohesive material. Both the low adhesion coating and the pad are optional in the combination and method of manufacturing the combination according to the present invention. In addition, the windows formed in the carrier are optional. If present, the carrier material in the area of the windows may remain in place or be removed as discussed above.

The next steps in the depicted method include converting the adhesive composite web into dressings and packaging the dressings. The web is preferably directed into a rotary die sheeting station which cuts the dressings out of the web in step 56 and removes any weed or waste material for disposal. The dressings can then be fed into a packaging step 58 in which the dressings are laminated between a top sheet and bottom sheet of packaging material. Packaging step 58 preferably uses packaging materials including a cohesive material (described above) that bonds the top and bottom sheets together around each dressing. In addition, the cohesive material on the release surface comprising a separate liner is preferably bonded to the cohesive material on the bottom sheet of the packaging material. Alternate mechanisms of attaching the packaging sheets to each other and providing a release surface on the bottom sheet of the package are discussed above.

The composite, now consisting of top package sheet/carrier/low adhesion coating/backing/backing adhesive/pad/release liner/bottom package sheet, is fed into a package sheeting station (preferably rotary die) to perform the step 60 of sheeting the web into individual packages.

It will be understood that there are alternate methods of accomplishing step 40, i.e., providing the backing/backing (pressure sensitive) adhesive/waste liner composite used in step 40 described above. In one alternative, the backing may be extruded or coated on a waste carrier to form a backing/waste carrier composite. The backing adhesive can then be coated on the waste liner to form a backing adhesive/liner composite. The backing adhesive/waste liner composite can then be laminated to the backing/waste carrier composite to form a waste carrier/backing/backing adhesive/waste liner composite. Finally, the waste carrier can be removed from the backing to provide a composite comprising the backing/backing (pressure sensitive) adhesive/waste liner composite material which can then be processed as described in the method of FIG. 4.

In another method of providing the backing/backing (pressure sensitive) adhesive/waste liner composite, the backing adhesive is coated on the waste liner and the backing material is extruded or coated directly onto the pressure sensitive adhesive to provide a backing/backing (pressure sensitive) adhesive/liner composite material. This second method is somewhat advantageous because it avoids the use of a waste carrier to reduce product costs and processing steps. Both methods and others are, however, contemplated for use in the methods according to the present invention.

Figure 5:
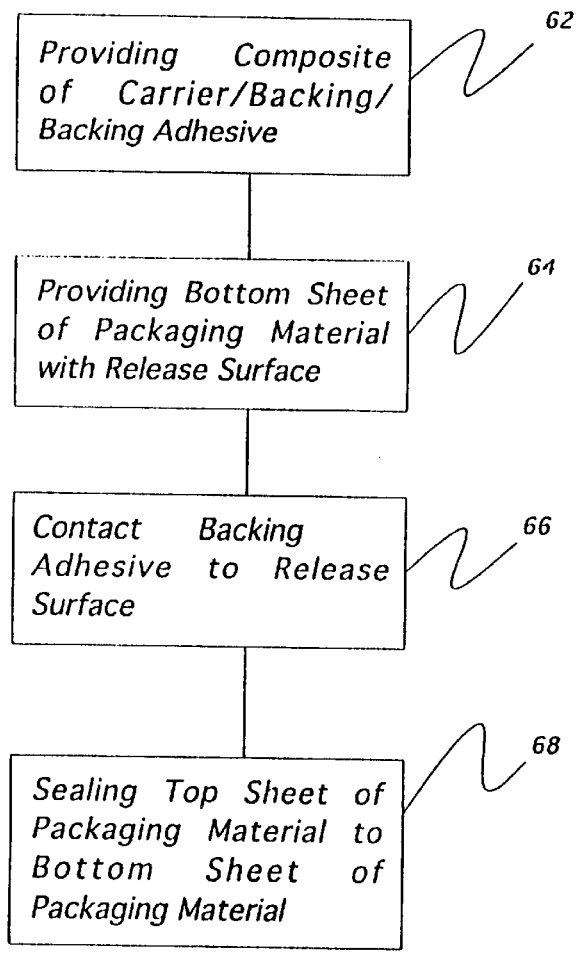
FIG. 5 is a flow chart depicting the steps in one method of manufacturing the dressing and package combination according to the present invention.

FIG. 5 is a block diagram of a more simplified method according to the present invention. Initial step 62 includes providing an adhesive dressing composite comprising a carrier/backing/backing adhesive. This composite can be in the form of a continuous web or in the form of individual dressings. The carrier, backing and adhesives can be provided of any suitable combination of materials as described above. Step 64 includes providing a bottom sheet of packaging material including a release surface. The release surface can be a coating on the bottom sheet or it can be located on a separate liner that is attached to the bottom sheet. Step 66 includes contacting the adhesive side of the composite with the release surface. Step 68 includes sealing a top sheet of packaging material over the composite and bottom sheet. Although one order for the above steps is depicted in FIG. 5, it will be understood that the steps may take place in any suitable order. For example, a release liner may first be contacted with the adhesive and later attached to the bottom sheet of the packaging material to complete the step 64 of providing a bottom sheet of packaging material with a release surface (see the method described in FIG. 4 for that approach).

Figure 6:
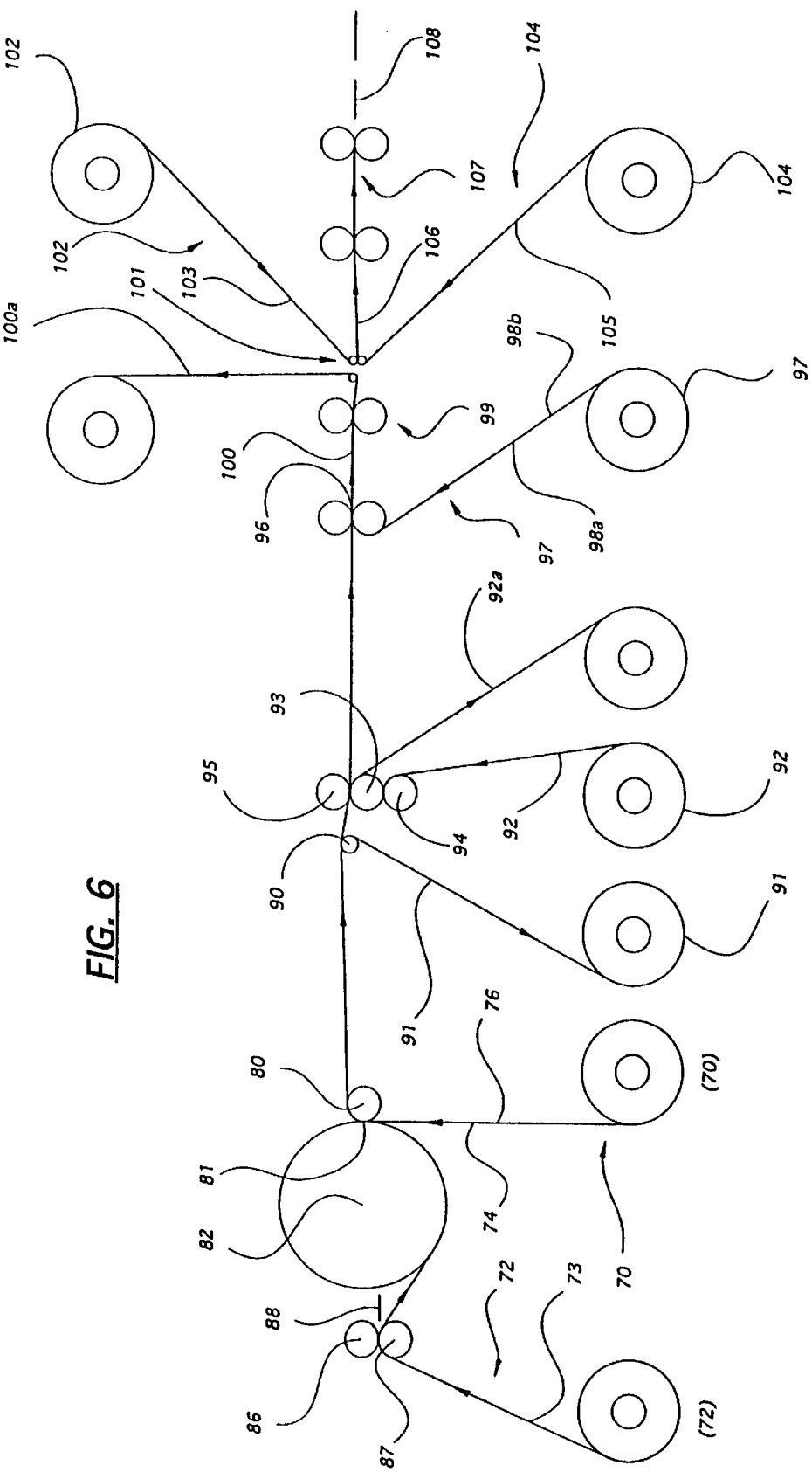
FIG. 6 is a schematic diagram of one method of manufacturing one dressing and package combination according to the present invention.

FIG. 6 depicts one schematic diagram of web fed rotary processing equipment that can be used to produce one dressing and package combination according to the present invention. The details of designing such equipment will be well known to those skilled in the art. Commercially available rotary web processing equipment, including control depth die cut systems, useful for practicing the method of the present invention can be obtained from, for example, the Mark Andy Company (St. Louis, Mo.) and Bernal Rotary Systems (Troy, Mich.).

Turning to FIG. 6, roll 72 preferably comprises a heat sealable carrier material (also designated 72), as described above, with the heat seal side 73 threaded as shown. The carrier material 72 is wrapped around a heated roll 82 as shown. The second input roll 70 comprises the low adhesion coating/backing/backing (pressure sensitive) adhesive/waste liner composite (also 70) according to the present invention. It will be understood that the low adhesion coating is optional. The low adhesion coating/backing portion 74 is wound out and the waste liner 76 is wound in as shown. The web from input roll 70 is threaded between the nip 81 formed between nip roll 80 and heated roll 82.

Die cut roll 86 and anvil roll 87 die cut the carrier material 72 to form windows in the carrier material 72 before it is heat sealed to the low adhesion coating/backing/backing (pressure sensitive) adhesive/waste liner composite 70. The windows 88 can be removed using a variety of means as discussed above. It will be understood that the windows could alternatively be control depth die cut in the carrier material 72 after the heat seal operation performed in nip 81. If the windows are removed after heat sealing, the heated roll 82 may include cavities (not shown) disposed around its perimeter to avoid heat sealing areas in the web corresponding to windows in the finished dressings as the web exits the heated roll nip 81. In a further alternative, no windows could be provided in the carrier material.

The composite web of carrier/low adhesion coating/backing/backing adhesive/waste liner is then passed over a knife edge 90 at which the waste liner 91 is removed from the composite web to expose the backing adhesive. With the backing adhesive exposed, pads can be attached to the composite web. Input roll 92 provides the pad material (also 92) to a die roll 93 which bears against anvil roll 94 to cut the desired pads (not shown) out of the pad material web 92. The pads are then placed on the backing adhesive using a nip between the die roll 93 and a backing roll 95. The weed 92a of unused pad material is then removed and discarded.

The composite web now comprises carrier/low adhesion coating/backing/backing adhesive/pads (although it will be understood that the low adhesion coating and pads are optional) and that composite web is fed into nip 96. Input roll 97 provides the release liner (also 97) which is also fed into nip 96 with the release surface 98a facing the backing adhesive. The opposite side of the release liner 97 is preferably coated with a cohesive material 98b that is used to bond the release liner 97 to the bottom sheet of the packaging material (as described above). After nip 96, the composite web 100 now includes carrier/low adhesion coating/backing/backing adhesive/pads/release liner/cohesive material.

The composite web 100 is fed into sheeting station 99 to cut the web 100 into the desired discrete dressings (not shown) and the weed 100a from that sheeting action is removed and discarded. The dressings are preferably immediately fed into a packaging nip 101. Input roll 102 feeds a top sheet (also 102) of packaging material into the packaging nip 101 and input roll 104 feeds a bottom sheet (also 104) of packaging material into the station 101. Top sheet 102 preferably includes a cohesive material 103 and bottom sheet 104 preferably includes cohesive material 105 which, when pressed together, bond to each other to seal the dressings between the top and bottom sheets 102 and 104. Also, where the release liner 97 includes compatible cohesive material 98b, the release liner material on the dressings bonds to the bottom sheet 104.

The composite web 106 now comprises discrete dressings located between top and bottom sheets of packaging material. That web 106 is then fed into a sheeting station 107 (preferably rotary die) where the packaged dressings 108 are separated for further processing, such as sterilization.

Figure 7:
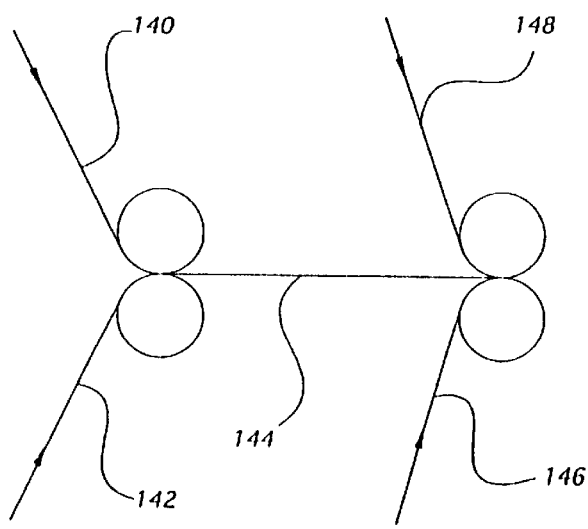
FIG. 7 is a schematic diagram of an alternate method of manufacturing one dressing and package combination according to the present invention.

FIG. 7 depicts an alternative schematic diagram of web fed rotary processing equipment that can be used to produce a dressing and package combination according to the present invention. As shown, the manufacturing line includes a supply of an adhesive dressing composite web 140 that includes the following components: carrier/backing/adhesive.

The web 140 is contacted with a release liner 142 such that the adhesive surface of the web 140 is in contact with a release surface on the release liner. If desired, it will be understood that pads could be placed on the adhesive of web 140 before the release liner 142 is contacted with the adhesive of composite web 140. One method of providing pads on an adhesive web surface is described in connection with FIG. 6 above. The composite 144 now includes at least the following components: carrier/backing/adhesive/release liner.

The release liner 142 is then attached to the bottom sheet of packaging material 146. It is preferred, but not required, that the dressings be separated, e.g., die cut, from the carrier/backing/adhesive/release liner composite 144 before the release liner 142 is attached to the bottom sheet 146. As discussed above, it is also preferred that the release liner 142 be attached to the bottom sheet 146 with a bond that is stronger than the bond between the release liner 142 and the adhesive on the backing. In one method of attaching the release liner 142 to the bottom sheet 146, the side of release liner 142 opposite the release surface is coated with a cohesive material that bonds with a cohesive material on the bottom sheet 146 of the packaging material to effect the desired bond. Other methods of attaching the release liner 142 to the bottom sheet of packaging material 146 are discussed above.

As shown in FIG. 7, the top sheet of packaging material 148 is also attached to the bottom sheet of packaging material 146 at the same station where the release liner 142 is attached to the bottom sheet of packaging material 146. This process is useful where the bond between the release liner 142 and bottom sheet 146 and the bond between the top sheet 148 and bottom sheet 146 are made using, for example, the cohesive materials described above. It will be understood that, depending on the actual mechanism used to form those bonds, the actual steps of attaching those components may take place at the same station or at different, i.e., sequential, stations. For example, the release liner 142 may be attached to the bottom sheet 146 at one station after which the top sheet 148 is attached to the bottom sheet 146 to form a package around each dressing.

Figure 8:
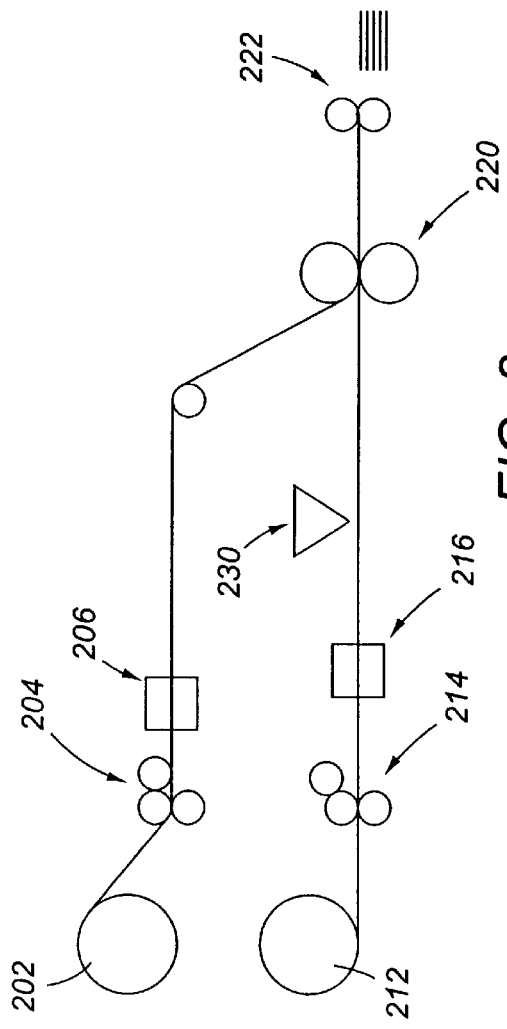
FIG. 8 is a schematic diagram of an alternate method of manufacturing one dressing and package combination according to the present invention.

Turning now to FIG. 8, an alternate method of manufacturing packaged medical adhesive composites according to the present invention will be described. The method includes supplying a roll of top sheet packaging material 202 and a roll of bottom sheet packaging material 212. Both the top and bottom sheet materials 202 and 212 are preferably provided with a cohesive material that will allow the two materials 202 and 212 to form a sealed package.

The top sheet packaging material 202 is directed through a printing station 204 in which graphics, product information, etc. can be applied to the web followed by a drying or curing station 206 for those printing processes that require drying or curing. The printed web is then directed into nip station 220.

The bottom sheet packaging material 212 is directed through a printing station 214 where the adhesive on the upper surface of the material 212 is coated with a release material as described above. One example of a suitable release material is a 100% solid ultraviolet curable silicone material. Others will be known to those skilled in the art. After the release areas have been formed on the web, it is directed into a drying or curing station 216, as needed. Following completion of the release areas, the web is then directed into a station 230 in which the medical adhesive composites are located on the release areas of the web.

After the medical adhesive composites have been located on the release surfaces on the bottom sheet packaging material, the web (with medical adhesive composites) is directed into the nip station 220 to seal the top and bottom sheets of the package together, thereby forming a seal around each of the medical adhesive composites. The web, now including top and bottom sheets encasing the medical adhesive composites, is then preferably directed into a sheeting station 222 where the packaged products are separated into the desired discrete packages.

Figure 9:
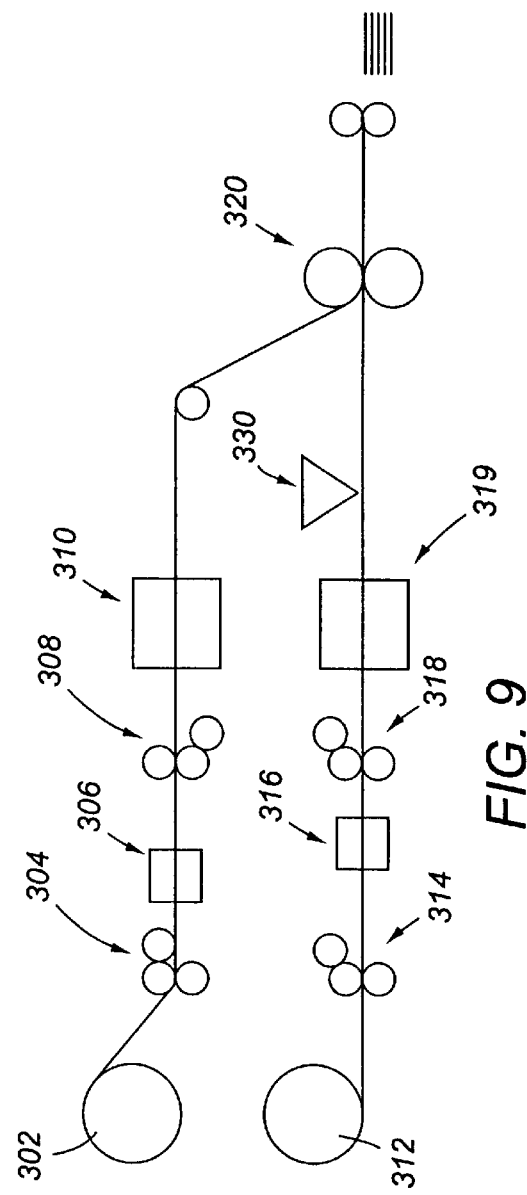
FIG. 9 is a schematic diagram of an alternate method of manufacturing one dressing and package combination according to the present invention.

Another method of manufacturing packaged medical adhesive composites according to the present invention will be described in connection with FIG. 9. The method includes supplying a roll of top sheet packaging material 302 and a roll of bottom sheet packaging material 312. In the depicted method, it is preferred to use either a contact adhesive or pressure sensitive adhesive to seal the top and bottom sheets of packaging material together. In this method, the top and bottom sheet materials 302 and 312 are preferably provided free of any adhesive coatings or layers needed to provide the desired sealed packages. Those materials will be coated in line as described below.

The web of bottom packaging material 312 is directed into a coating station 314 in which a release material is printed or otherwise coated on the upper surface of the web 312. The release material coated or otherwise applied at station 314 forms the release surfaces of the package as described above. After the release material is applied at station 314, the web 312 can be directed into a drying or curing station 316 to dry or cure the release material if required.

After station 316, the web 312 with release material is directed into station 318 where a contact adhesive or pressure sensitive adhesive is applied to the upper surface of the web 312. In the depicted method, it may be preferred to print the adhesive using, e.g., a rubber plate printing station, a rotary screen printer, or other suitable process. Regardless of the actual material being applied, it is preferred that the adhesive be applied to the web 312 in a pattern in which the adhesive frames or outlines the dressings to be packaged.

After the adhesive coating station 318, the adhesive coated web 312 can be directed into a drying or curing station 319 to dry or cure the adhesive coated on the web 312 in station 318. Following drying or curing, the web 312 is directed into station 330 where the medical adhesive composites are located on the release surface formed in stations 314 and 316. After the medical adhesive composites are located in station 330, the web 312 is directed into the nip station 320.

Turning to the top sheet, the web of packaging material 302 can be directed through a printing station 304 in which graphics, product information, etc. can be applied to the web 302. After the printing in station 304, the web 302 can be directed into a drying or curing station 306 for those printing processes that require drying or curing.

The printed web 302 is then directed into a second coating station 308 in which a contact adhesive can be applied to the underside of the web 302. In the depicted method, it may be preferred to print an adhesive coating on the underside of the web 302. The contact adhesive can be applied by a rubber plate printing station, a rotary screen printer, or other suitable process. The adhesive can be applied over the entire surface of the web 302, but is preferably applied in a pattern that frames or outlines the medical adhesive composites to be packaged.

After the adhesive coating station 308, the web 302 can be directed into a drying or curing station 310 to dry or cure the adhesive coated on the web 302 in station 308. Following drying or curing, the web 302 is directed into the nip station 320.

It will be understood that the second coating station 308 and its companion drying or curing station 310 are optional and may be removed if the bottom sheet of packaging material 312 is coated with a pressure sensitive adhesive as opposed to a contact adhesive (which by its very nature requires that both surfaces to be joined be coated with the contact adhesive). When web 312 is coated with a pressure sensitive adhesive, however, the top sheet of packaging material 302 need only be forced against the pressure sensitive adhesive in order to form the desired seal.

It will be understood by those skilled in the art that the schematic diagrams provided in FIGS. 6–9 represent potential equipment configurations only and should not be construed as limiting the methods of the present invention, which are defined in the claims appended hereto. For example, referring to the process depicted in FIG. 6, it would be possible to provide a station for applying a release material on the preferred cohesive material 105 provided on the bottom sheet of packaging material unwound from roll 104. Likewise, a printing station could also be located to print the desired graphics, product information, etc. on the top sheet of packaging material being unwound from roll 102. In a similar manner, printing and coating stations could also be supplied in the process depicted in FIG. 7.

The integration of process steps such as printing the top sheets, applying the adhesive, release materials, etc. provides a distinct advantage in that a "make-in-place" system can be developed to reduce the inventory of packaging materials typically required for packaging a variety of different products. Typically, the packaging webs must be coated with adhesives or printed with product information in separate steps, thereby creating an inventory of those products. In at least some of the more integrated methods described above, the packaging materials can be provided plain, i.e., free of any adhesives, cohesive materials, and/or printed information. As a result, only the basic packaging materials need to be maintained in inventory and those unfinished materials can then be finished in line with the packaging processes (and in some cases the product may also be manufactured in line as well, see, e.g., FIG. 6).

After the individual packaged products are produced, they will typically be sterilized, particularly in the case of dressings, bandages, etc. Those skilled in the art will understand that sterilization of the resulting products can also affect the bond strength. In particular, it is known that the strength of the bond between the preferred backing adhesive and a patient's skin is affected by gamma sterilization. Gamma sterilization also has been found to have some effect in strengthening heat seal bonds, but the effect is much less pronounced than the effect on the backing adhesive/skin bond strength. These variations should be considered when selecting any adhesives, heat seal materials, and release agents to be used in connection with the present invention to ensure that the final product, i.e., the dressing and package combination has the desired relative bond strengths as discussed above to ensure proper functioning of the product.

One potentially useful apparatus for practicing at least some of the methods according to the present invention is disclosed in commonly-assigned U.S. patent application Ser. No. 08/442,823, filed on May 17, 1996, titled ROTARY DRUM CONVERTER, by J. Riedel and C. Niven.

The following non-limiting examples will further illustrate the articles and methods of the present invention. All parts and percentages are expressed as parts by weight unless otherwise indicated.

EXAMPLE 1

A pressure sensitive adhesive prepared in accordance with U.S. Pat. No. 4,737,410 (Example 31) comprising a terpolymer of 70% units of isooctyl acrylate, 16% units of ethyleneoxide acrylate, and 14% units of acrylic acid was applied at a coating weight of 33.5 grams per square meter to one side of a 60 pound two side coated release liner (2-60BKG-157-99AM; Daubert Coated Products, Inc., Willowbrook, Ill.) using a horizontal knife coater.

A 1.2 mil (30 micrometer) thick film of Estane 58309NAT022 polyurethane resin (B. F. Goodrich, Cleveland, Ohio) was laminated to the adhesive surface to form the backing for the dressings.

A low adhesion back coating was gravure-coated on the backing using a 200 line pyramid knurled roll and dried. The solution used was 6% solids (20 parts silicone and 80 parts polyvinyl N-octadecyl carbamate) comprising: 1) a silicone resin blend of SS4300 at 95% units and SR-0545 at 5% units, both from General Electric (Waterford, N.Y.), the blend provided in 90% (by weight) toluene; and 2) a backsizing solution in accordance with U.S. Pat. No. 2,532,011, comprising polyvinyl N-octadecyl carbamate 5% solids in xylene-toluene (22%–78% by weight).

The resulting low adhesion coating/backing/adhesive/liner composite was slit to the desired width.

A carrier material (1-80BKG-157 & PE; Daubert Coated Products, Inc.) was die cut to form windows which were then removed. The polyethylene (PE) side of the carrier material was then heat laminated to the backing over the low adhesion coating in accordance with methods taught in U.S. Pat. No. 5,531,855.

The liner (Daubert 2-60BKG-157-99AM) was then removed and replaced with a product liner having a release coated surface and a cohesive material coated surface. The product liner was made from 25# Rinelander medical kraft paper (Phoenix Products Company, Inc. Milwaukee, Wis.) coated on one side with a cohesive coating formulated per Phoenix Stock #PHX-3006 at a coating weight of 2.4–4.0 grams per square meter (1.5–2.5 pounds per 3000 square feet). The opposite side of the product liner was coated with an ultra-violet light cured silicone coating commercially available from Douglas-Hanson Company, Hammond, Wis. at a coating weight of 1.5–2.5 grams per square meter.

The composite of carrier/low adhesion coating/backing/backing adhesive/product liner was sheeted into dressings using rotary die cutting equipment and placed into cold seal packaging supplied by Phoenix Products Company. The package included two layers, one coated with anchor coating per Phoenix Products Company Stock #PHX-3023 and the other coated with transfer coating per Phoenix Products Company Stock #PHX-3006. The cold seal side of the adhesive covering the product liner bonded readily to the packaging without additional processing steps. The finished bandages were subsequently radiation sterilized and checked for function. The package peels opened normally and the bandage was removed easily from the adhesive covering that had become attached to the packaging material, allowing delivery of the product from the package using the frame carrier with the adhesive surface exposed and ready to apply to the skin.

EXAMPLE 2

An 8 inch by 10 inch (0.20 meter by 0.25 meter) sample of one side coated silicone release liner identified as Akrosil BL 19 MGH SILOX C3R/0 commercially available from International Paper Company, Menasha, Wis. was coated with cohesive material formulated per Phoenix stock #PHX-3006 by Phoenix Products Company. The resulting double-side coated product release liner/cold seal was used to make samples similar to those described in Example 1 substituting only the aforementioned release liner/cold seal paper. Results were equivalent to those of Example 1. These samples were not irradiated.

EXAMPLE 3

An 8 inch by 10 inch (0.20 meter by 0.25 meter) sample of one side coated silicone release liner identified as ESP-43 reference 48889 manufactured by Lohjan Paperi Oy, Lohia, Finland commercially available through Daubert Coated Products, Inc. was coated with cohesive material formulated per Phoenix stock #PHX-3006 by Phoenix Products Company. The resulting double-side coated product release liner/cold seal was used to make samples similar to those described in Example 1 substituting only the aforementioned release liner/cold seal paper. Results were equivalent to Example 1. These samples were not irradiated.

EXAMPLE 4

A 6 inch by 36 inch (0.15 meter by 0.91 meter) sample of one side coated silicone release liner identified as ESP-48 manufactured by Lohjan Paperi Oy, Lohia, Finland commercially available through Daubert Coated Products, Inc. was coated with cohesive material formulated by diluting Sanford Rubber Cement available from Sanford Corporation, Bellwood, Ill., weight to weight 50% with heptane. The resulting double-side coated product release liner/cold seal was used to make samples similar to those described in Example 1 substituting only the aforementioned release liner/cold seal paper. Results were equivalent to Example 1. These samples were not irradiated.

EXAMPLE 5

A sample of the packaging material of Example 1 (4 inches by 10 yards/0.1 meters by 9 meters) was full surface coated with a cohesive material Phoenix Products Company Stock #PHX-3023. An offset printing process was then used to apply a release material over the cohesive material at a 3% solids level (resulting in a coating weight of about 1.1 grams per square meter) to supply the desired release areas. The release areas were rectangular (each 3 centimeters by 9.5 centimeters) and the release material used was UV-9300, available from GE Silicones. After the release material was in place, it was exposed to ultraviolet energy to provide satisfactory release characteristics.

A medical adhesive composite dressing of the proper dimensions for the release areas was applied to each of a number of these release areas, with the pressure sensitive adhesive releasably adhered to the release areas.

A top sheet of packaging material coated with a layer of cohesive material (Phoenix stock #PHX-3006 by Phoenix Products Company) was then applied over the bottom sheet of packaging material and medical adhesive composites to form packages. The packages were then irradiated for sterilization. The irradiated packages were then opened and the product was removed from the release areas with satisfactory results.

EXAMPLE 6

A sample was prepared in a fashion similar to that used in Example 5 except that the release material used for the release areas was UV-9315 available from GE Silicones. The release material was applied with a rotogravure roller and doctor blade that resulted in a coating weight of 1.95 grams per square meter. The release areas formed were rectangular (2.5 centimeters by 7 centimeters). Performance of the completed packages was also satisfactory.

All patents, patent applications, and publications cited herein are each incorporated herein by reference in their entirety, as if individually incorporated by reference. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for making a combination of a medical adhesive composite in a package comprising the steps of:
   (a) providing a medical adhesive composite including a substrate having top and bottom faces and a pressure sensitive adhesive on the bottom face of the substrate;
   (b) providing a bottom sheet of packaging material having a cohesive material located thereon;
   (c) providing a release surface between the bottom sheet of packaging material and the adhesive on the bottom face of the substrate, the release surface comprising a release coating applied over a portion of the cohesive material on the bottom sheet, wherein the bond between the release coating and the cohesive material on the bottom sheet is stronger than the bond between the release coating and the adhesive;
   (d) providing a top sheet of packaging material over the medical adhesive composite, the top sheet including a cohesive material located thereon, wherein the medical adhesive composite is located between the top and bottom sheets; and
   (e) sealing the top sheet to the bottom sheet about the periphery of the medical adhesive composite using the cohesive material on the top and bottom sheets of packaging material.

2. The method of claim 1, further comprising attaching a carrier to at least a portion of the top face of the substrate.

3. The method of claim 2, wherein the step of attaching a carrier comprises attaching the carrier to at least a substantial portion of the periphery of the substrate.

4. The method of claim 2, wherein the step of attaching a carrier comprises attaching the carrier to substantially the entire top face of the substrate.

5. The method of claim 2, wherein the step of attaching a carrier comprises attaching two opposing portions of carrier on opposing sides of the substrate.

6. A method of using a combination adhesive composite dressing and package comprising the steps of:
   (a) providing a combination comprising:
      (1) medical adhesive composite comprising:
         (A) a substrate having top and bottom faces;
         (B) a pressure sensitive adhesive coated on at least a portion of the bottom face of the substrate; and
      (2) a package housing the medical adhesive composite comprising:
         (A) a top sheet located over the top face of the substrate, the top sheet including a layer of cohesive material on at least a portion of the top sheet;
         (B) a bottom sheet located under the adhesive on the bottom face of the substrate, the bottom sheet comprising a layer of cohesive material located over substantially all of the bottom sheet, wherein the medical adhesive composite is located between the top and bottom sheets, and further wherein the top and bottom sheets are sealed to each other about the periphery of the medical adhesive composite by the layers of cohesive material on the top and bottom sheets; and
         (C) a release surface at least as large as the pressure sensitive adhesive, the release surface comprising a release coating applied over a portion of the layer of cohesive material on the bottom sheet, wherein the bond strength between the release coating and the cohesive material on the bottom sheet is greater than the bond strength between the release coating and the adhesive on the bottom face of the medical adhesive composite;
   (b) separating at least a portion of the top sheet from the bottom sheet to expose the medical adhesive composite;
   (c) separating the adhesive on the bottom face of the substrate from the release surface, wherein the medical adhesive composite is removed from the bottom sheet of the packaging material;
   (d) applying the adhesive and attached substrate to a patient.

7. The method of claim 6, wherein the medical adhesive composite further comprises a carrier attached to at least a portion of the top face of the substrate.

8. The method of claim 7, further comprising the step of removing the carrier from the substrate after the substrate is attached to a patient.

9. A combination of a medical adhesive composite in a package comprising:
   (a) a medical adhesive composite comprising:
      (1) a substrate having top and bottom faces;
      (2) a pressure sensitive adhesive coated on at least a portion of the bottom face of the substrate; and
   (b) a package housing the medical adhesive composite comprising:
      (1) a top sheet located over the top face of the substrate of the medical adhesive composite;
      (2) a bottom sheet located under the adhesive on the medical adhesive composite;
      (3) cohesive material on at least a portion of the top sheet and over substantially all of the bottom sheet, the cohesive material on the top sheet being opposed to and facing cohesive material on the bottom sheet, wherein the top and bottom sheets are sealed to each other about the periphery of the medical adhesive composite by the cohesive material; and
      (4) a release surface at least as large as the pressure sensitive adhesive on the medical adhesive composite, the release surface comprising a release coating applied over the cohesive material on the bottom sheet, wherein the bond strength between the release coating and the cohesive material on the bottom sheet is greater than the bond strength between the release coating and the adhesive on the medical adhesive composite.

10. The combination of claim 9, further comprising a carrier attached to at least a portion of the top face of the substrate.

11. The combination of claim 10, wherein the carrier is heat sealed to the substrate.

12. The combination of claim 10, wherein the bond strength between the carrier and the substrate is greater than the bond strength between the adhesive on the bottom face of the substrate and the release surface.

13. The combination of claim 10, wherein the bond strength between carrier and the substrate is less than the bond strength between the adhesive on the substrate and the skin of a patient.

14. The combination of claim 10, wherein the carrier is attached to at least a substantial portion of the periphery of the substrate.

15. The combination of claim 10, wherein the carrier is attached to substantially the entire top face of the substrate.

16. The combination of claim 10, wherein the carrier comprises two opposing portions located on opposing sides of the substrate.

17. The combination of claim 10, wherein the substrate comprises a conformable elastomeric film.

18. The combination of claim 17, wherein the substrate is selected from the group consisting of polyurethane film, polyester film, polyether block amide film and combinations thereof.

19. The combination of claim 9, wherein the medical adhesive composite further comprises a pad positioned on the bottom face of the substrate.

20. The combination of claim 19, wherein the pad contains one or more substances selected from the group consisting of antimicrobial agents, drugs, chemical indicators, and combinations thereof.

21. A method for making a combination of an adhesive composite dressing in a package comprising the steps of:
   (a) providing a composite dressing including a backing having top and bottom faces and a pressure sensitive adhesive on the bottom face of the backing;
   (b) attaching a carrier to at least a portion of the top face of the backing, the carrier supporting the backing;
   (c) providing a bottom sheet of packaging material;
   (d) providing a release surface between the bottom sheet of packaging material and the adhesive on the bottom face of the backing, the release surface attached to the bottom sheet, wherein the bond between the release surface and the bottom sheet is stronger than the bond between the release surface and the adhesive;
   (e) providing a top sheet of packaging material over the composite dressing wherein the composite dressing is located between the top and bottom sheets;
   (f) sealing the top sheet to the bottom sheet about the periphery of the composite dressing; and
   (g) printing production information on at least one of the top and bottom sheets of packaging material, the printing being performed in-line with the steps of sealing the top and bottom sheets of packaging material and sealing the top and bottom sheets.

22. The method of claim 21, wherein the step of providing a release surface comprises providing a release liner comprising the release surface, the release liner attached to the bottom sheet of packaging material.

23. The method of claim 21, wherein the step of providing a release surface comprises providing a release coating on the bottom sheet of the packaging material.

24. The method of claim 23, wherein the step of attaching a carrier comprises attaching the carrier to at least a substantial portion of the periphery of the backing.

25. The method of claim 21, wherein the step of attaching a carrier comprises attaching the carrier to substantially the entire top face of the backing.

26. The method of claim 21, wherein the step of attaching a carrier comprises attaching two opposing portions of carrier on opposing sides of the backing.

* * * * *